United States Patent
Vangara et al.

(10) Patent No.: US 12,303,599 B2
(45) Date of Patent: *May 20, 2025

(54) SELF-EMULSIFYING CANNABIDIOL FORMULATIONS

(71) Applicant: Benuvia Operations, LLC, Round Rock, TX (US)

(72) Inventors: Kiran Kumar Vangara, Phoenix, AZ (US); Thrimoorthy Potta, Phoenix, AZ (US); Venkat Goskonda, Phoenix, AZ (US)

(73) Assignee: Benuvia Operations, LLC, Round Rock, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/534,301

(22) Filed: Dec. 8, 2023

(65) Prior Publication Data

US 2024/0099971 A1 Mar. 28, 2024

Related U.S. Application Data

(63) Continuation of application No. 16/874,225, filed on May 14, 2020, now Pat. No. 11,857,678.

(60) Provisional application No. 62/847,991, filed on May 15, 2019.

(51) Int. Cl.
| | | |
|---|---|---|
| *A61K 9/107* | (2006.01) | |
| *A61K 9/48* | (2006.01) | |
| *A61K 31/05* | (2006.01) | |
| *A61K 47/10* | (2017.01) | |
| *A61K 47/14* | (2017.01) | |
| *A61K 47/22* | (2006.01) | |

(52) U.S. Cl.
CPC ............ *A61K 9/107* (2013.01); *A61K 9/4808* (2013.01); *A61K 9/4825* (2013.01); *A61K 31/05* (2013.01); *A61K 47/10* (2013.01); *A61K 47/14* (2013.01); *A61K 47/22* (2013.01)

(58) Field of Classification Search
CPC .... A61K 9/107; A61K 9/4808; A61K 9/4825; A61K 31/05; A61K 47/10; A61K 47/14; A61K 47/22; A61K 9/1075; A61K 9/4858; A61K 47/44
See application file for complete search history.

(56) References Cited

U.S. PATENT DOCUMENTS

| | | |
|---|---|---|
| 2014/0357708 A1 | 12/2014 | Murty et al. |
| 2016/0184258 A1 | 6/2016 | Murty et al. |
| 2018/0169061 A1 | 6/2018 | Gumudavelli et al. |
| 2019/0015346 A1 | 1/2019 | Diorio |

FOREIGN PATENT DOCUMENTS

| | | |
|---|---|---|
| CA | 2952335 A1 | 6/2017 |
| WO | 2017149392 A1 | 9/2017 |
| WO | 2018011808 A1 | 1/2018 |

OTHER PUBLICATIONS

International Preliminary Report on Patentability; International Application No. PCT/IB2020/000610, filed May 14, 2020; Mailing Date Nov. 16, 2021.
International Search Report; International Application No. PCT/IB2020/000610, filed May 14, 2020; Mailing Date Mar. 22, 2021. (3 pages).
Written Opinion; International Application No. PCT/IB2020/000610, filed May 14, 2020; Mailing Date Mar. 22, 2021. (8 pages).

*Primary Examiner* — Robert A Wax
*Assistant Examiner* — Quanglong N Truong
(74) *Attorney, Agent, or Firm* — Jason T. Daniel, Esq.; Daniel Law Offices, P.A.

(57) ABSTRACT

The present invention is directed to a self-emulsifying cannabidiol composition containing one or more surfactants. The present invention is further directed to a method of treating a disease comprising administering a composition of the present invention to a subject in need thereof. The present invention is further directed to a method of treating withdrawal symptoms.

18 Claims, 1 Drawing Sheet

SELF-EMULSIFYING CANNABIDIOL FORMULATIONS

CROSS-REFERENCE TO RELATED APPLICATIONS

This application is a continuation of and claims priority to U.S. application Ser. No. 16/874,225 filed May 15, 2020, and U.S. Application Ser. No. 62/847,991, filed May 15, 2019. The entire contents of each of which are hereby incorporated by reference in their entirety.

FIELD OF THE INVENTION

The present invention is directed to a self-emulsifying cannabidiol composition containing one or more surfactants. The present invention is further directed to a method of treating a disease comprising administering a composition of the present invention to a subject in need thereof. The present invention is further directed to a method of treating withdrawal symptoms comprising administering a composition of the present invention to a subject in need thereof.

BACKGROUND

Cannabidiol, (–)-trans-2-p-mentha-1,8-dien-3-yl-5-pentylresorcinol, is non-psychoactive and has shown promise in treating numerous diseases and disorders. Cannabidiol has been approved by the United States Food and Drug Administration for to treat Lennox-Gastaut syndrome, Dravet syndrome. Further, cannabidiol, may be suitable for the treatment of diseases or disorders, or symptoms of diseases or disorders, such as mycolonic seizures, juvenile mycolonic epilepsy, refractory epilepsy, schizophrenia, juvenile spasms, West syndrome, refractory infantile spasms, infantile spasms, tubular sclerosis complex, brain tumors, neuropathic pain, *cannabis* use disorder, post-traumatic stress disorder, anxiety, early psychosis, Alzheimer's Disease autism, and withdrawal from opioids, cocaine, heroin, amphetamines, and nicotine.

While there are many dosage forms of cannabidiol the most popular form is oral. Oral formulations of cannabidiol are more convenient and are more likely to lead to patient compliance. Oral dosages of cannabidiol has been formulated in hydroalcoholic and lipid-based formulations. The issue with these oral formulations is that they have poor solubility and thus poor bioavailability in water such as encountered in the gastrointestinal tract when imbibed.

To combat poor solubility formulation scientist have developed Self-Emulsifying Drug Delivery system (SEDDS). SEDDS have shown to improve solubilization of poorly soluble drugs, improve the bioavailability due to reduced first pass metabolism and improved absorption through lymphatic transport by forming chylomicrons. However, developing a SEDDS is a painstaking task that differs for each active ingredient. The specific excipients and concentrations may only be discovered through intense formulation research.

Accordingly, there is a need in the art for a cannabidiol formulation that self emulsifies in contact with an aqueous medium.

SUMMARY OF THE INVENTION

The present invention is directed to a self-emulsifying cannabidiol composition comprising from about 1 to about 40% w/w cannabidiol and from about 40% to about 99% w/w of one or more surfactants selected from polyethylene glycol 40 hydrogenated castor oil, caprylocaproyl polyoxyl-8 glycerides, lauoryl polyoxylglycerides, oleoyl polyoxyl-6 glycerides, linoleoyl polyoxyl-6 glycerides, lauroyl polyoxyl-6 glycerides, propylene glycol monocaprylate, propylene glycol monolaurate, polyglyceryl-3 dioleate, a polysorbate and sorbitan monooeate.

The present invention is further directed to a self-emulsifying cannabidiol composition comprising:
  from about 5% to about 35% w/w cannabidiol;
  from about 2% to about 60% w/w polyethylene glycol 40 hydrogenated castor oil;
  from about 2% to about 50% w/w of a surfactant selected from caprylocaproyl polyoxyl-8 glycerides, linoleoyl polyoxyl-6 glyceride or a combination thereof; and
  from about 0.1% to about 2% w/w alpha tocopherol.

The present invention is further directed to a method of treating a disease selected from Prader-Willi syndrome, obesity, graft versus host disease, gelastic seizures/hypothalamic hamartoma, neonatal seizures, dystonia, central pain syndromes, phantom limb pain, multiple sclerosis, traumatic brain injury, radiation therapy, acute graft versus host disease, chronic graft versus host disease, T-cell autoimmune disorders, colitis, Dravet Syndrome, Lennox Gastaut Syndrome, mycolonic seizures, juvenile mycolonic epilepsy, refractory epilepsy, childhood absence epilepsy, schizophrenia, juvenile spasms, West syndrome, infantile spasms, refractory infantile spasms, tuberous sclerosis complex, brain tumors, neuropathic pain, *cannabis* use disorder, post-traumatic stress disorder, anxiety, early psychosis, Alzheimer's Disease, autism, acne, Parkinson's disease, social anxiety disorder, depression, diabetic retinopathy, diabetic nephropathy, diabetic neuropathy, ischemic injury of heart, ischemic injury of brain, chronic pain syndrome, and rheumatoid arthritis comprising administering a composition of the present invention to a subject in need thereof.

The present invention is further directed to a method of treating withdrawal symptoms comprising administering a composition of the present invention to a subject in need thereof, wherein the withdrawal symptoms are caused by the subject reducing or quitting use of an opioid, cocaine, heroin, an amphetamine or nicotine.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION OF THE INVENTION

Figure 1:
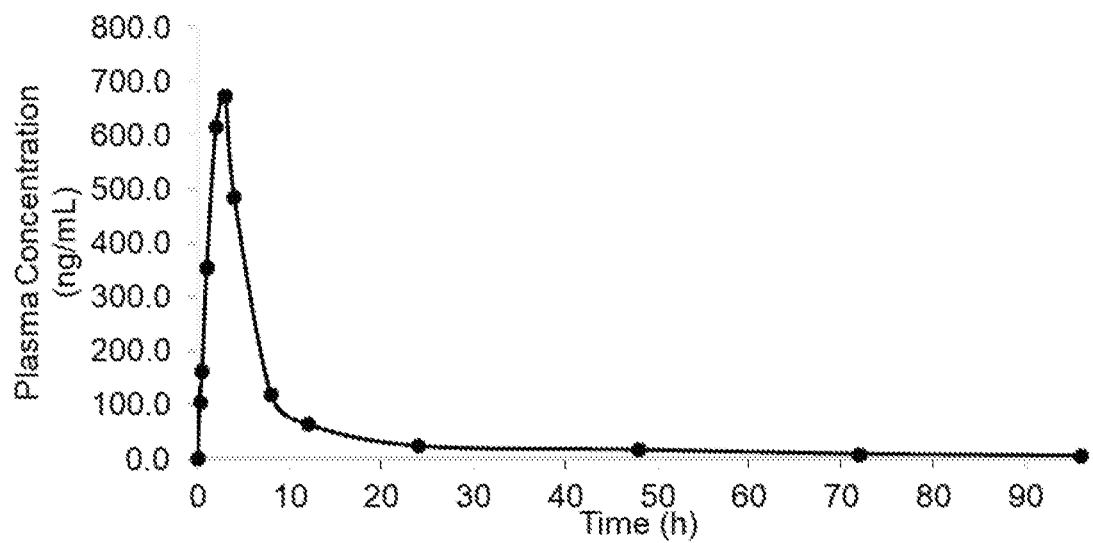
FIG. 1. Shows an illustration of plasma concentration of cannabidiol after administration of Composition 5 from time 0 to 96 hours.

The detailed description of exemplary embodiments herein makes reference to the accompanying drawings which show exemplary embodiments by way of illustration and their best mode. While these exemplary embodiments are described in sufficient detail to enable those skilled in the art to practice the inventions, it should be understood that other embodiments may be realized and that logical, chemical, and mechanical changes may be made without departing from the spirit and scope of the inventions. Thus, the detailed description herein is presented for purposes of illustration only and not of limitation. For example, the steps herein recited in any of the method of process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Applicant unexpectedly found that the presence of particular surfactants in a cannabidiol composition form an emulsion with an average globule size capable of passing through the gastrointestinal tract when dispersed in an aqueous medium.

In one embodiment, the present invention is directed to a self-emulsifying cannabidiol composition comprising from about 1 to about 40% w/w cannabidiol and from about 40% to about 99% w/w of one or more surfactants selected from polyethylene glycol ("PEG") 40 hydrogenated castor oil, caprylocaproyl polyoxyl-8 glycerides, lauroyl polyoxylglycerides, oleoyl polyoxyl-6 glycerides, linoleoyl polyoxyl-6 glycerides, lauroyl polyoxyl-6 glycerides, propylene glycol monocaprylate, propylene glycol monolaurate, polyglyceryl-3 dioleate, a polysorbate and sorbitan monooleate.

In a preferred embodiment, the present invention is further directed to a self-emulsifying cannabidiol composition comprising:
  from about 5% to about 35% w/w cannabidiol;
  from about 2% to about 60% w/w PEG 40 hydrogenated castor oil;
  from about 2% to about 50% w/w of a surfactant selected from caprylocaproyl polyoxyl-8 glycerides, linoleoyl polyoxyl-6 glyceride or a combination thereof; and
  from about 0.1% to about 2% w/w alpha tocopherol.

Cannabidiol may be present in compositions of the present invention at a concentration from about 0.1% to about 50% w/w, preferably from about 1% to about 40% w/w, more preferably from about 5% to about 35% w/w, even more preferably from about 10% to about 30% w/w or about 10% to about 20% w/w.

Surfactants suitable for use in the present invention include, but are not limited to, PEG 40 hydrogenated castor oil, caprylocaproyl polyoxyl-8 glycerides, lauroyl polyoxylglycerides, oleoyl polyoxyl-6 glycerides, linoleoyl polyoxyl-6 glycerides, lauroyl polyoxyl-6 glycerides, propylene glycol monocaprylate, propylene glycol monolaurate, polyglyceryl-3 dioleate, a polysorbate and sorbitan monooleate. In a preferred embodiment, surfactants may be selected from PEG 40 hydrogenated castor oil, caprylocaproyl polyoxyl-8 glycerides, linoleoyl polyoxyl-6 glycerides, polyglyceryl-3 dioleate, polysorbate 80 or a combination thereof.

The one or more surfactants may be present in compositions of the present invention at a concentration from about 1% to about 99% w/w, preferably from about 40% to about 99% or from about 2% to about 50% w/w, even more preferably from about 40% to about 80% w/w or from about 20% to about 40% w/w and yet even more preferably from about 44% to about 78% w/w.

Polyethylene glycol ("PEG") 40 hydrogenated castor oil may be present in compositions of the present invention at a concentration from about 2% to about 60% w/w, preferably from about 10% to about 50% w/w and more preferably from about 10% to about 40% w/w.

Polyglyceryl-3 dioleate may be present in compositions of the present invention at a concentration from about 1% to about 15% w/w, preferably from about 2% to about 12% w/w.

Caprylocaproyl polyoxyl-8 glycerides may be present in compositions of the present invention at a concentration from about 1% to about 30% w/w, more preferably from about 3% to about 26% w/w.

Linoleoyl polyoxyl-6 glycerides may be present in compositions of the present invention at a concentration from about 1% to about 30% w/w, more preferably from about 4% to about 23% w/w.

Polysorbate 80 may be present in compositions of the present invention at a concentration from about 1% to about 10% w/w, more preferably from about 2% to about 6% w/w.

Oils suitable for use in compositions of the present invention include, but are not limited to, glyceryl monolinoleate, glyceryl monooleate, propylene glycol dicaprylocaprate, glycerol monostearate 40-55, a medium chain triglyceride or a combination thereof. In a preferred embodiment, the oil is a medium chain triglyceride, preferably a C8/C10 medium chain triglyceride.

The one or more oils may be present in compositions of the present invention at a concentration from about 1% to about 50% w/w, preferably from about 5% to about 30% w/w, more preferably from about 5% to about 25% w/w.

Medium chain triglycerides may be present in compositions of the present invention at a concentration from about 1% to about 30% w/w, preferably from about 9% to about 24% w/w.

Cosolvents suitable for use in the present invention include, but are not limited to, propylene glycol, polyethylene glycol, ethanol or a combination thereof.

The one or more cosolvents may be present in compositions of the present invention at a concentration from about 1% to about 50% w/w, preferably from about 5% to about 30% w/w, even more preferably from about 12% to about 21% w/w.

Ethanol may be present in compositions of the present invention at a concentration from about 1% to about 20% w/w, preferably from about 5% to about 15% w/w, even more preferably from about 10% to about 15% w/w and most preferably from about 12% to about 14% w/w.

Propylene glycol may be present in compositions of the present invention at a concentration from about 1% to about 20% w/w, preferably from about 5% to about 15% w/w, even more preferably from about 5% to about 10% w/w and most preferably from about 8% to about 10% w/w.

Antioxidants suitable for use in the present invention include, but are not limited to, alpha tocopherol, butylated hydroxy anisole, butylated hydroxy toluene, ascorbyl palmitate, ascorbic acid, sodium ascorbate, sodium metabisulfite, EDTA, citric acid, sodium bisulfite, sodium thiosulfate, thioglycerol, propyl gallate or a combination thereof. In a preferred embodiment, the antioxidant is alpha tocopherol, ascorbyl palmitate or a combination thereof.

The one or more antioxidants may be present in compositions of the present invention at a concentration from about 0.01% to about 2% w/w, preferably from about 0.05% to about 1% w/w and even more preferably from about 0.1% to about 0.5% w/w.

Alpha tocopherol may be present in compositions of the present invention at a concentration from about 0.01% to about 2% w/w, preferably from about 0.01% to about 1% w/w, even more preferably from about 0.05% to about 0.5% w/w and yet more preferably from about 0.05% to about 0.4% w/w.

Ascorbyl palmitate may be present in compositions of the present invention at a concentration from about 0.01% to about 2% w/w, preferably from about 0.01% to about 1% w/w and even more preferably from about 0.05% to about 0.2% w/w.

In another embodiment, the composition of the present invention does not contain sesame oil, castor oil, olive oil or water.

In a preferred embodiment, the compositions of the present invention form an emulsion having an average globule size from about 20 to about 5,000 nanometers when dispersed in an aqueous medium, preferably from about 30 to about 600 nanometers, even more preferably from about 100 to about 1,000 nanometers and yet more preferably from about 100 to about 300 nanometers. In a more preferred embodiment, the aqueous medium is gastric fluid.

In another preferred embodiment, the compositions of the present invention emulsifies in less than 30 minutes upon contact with an aqueous medium including gastric fluid.

In another preferred embodiment, the compositions of the present invention are contained in a soft or a hard gelatin capsule.

In a most preferred embodiment, the present invention is directed to a self-emulsifying cannabidiol composition comprising:
  about 20.5% w/w cannabidiol;
  about 12.0% w/w ethanol;
  about 9.0% w/w propylene glycol;
  about 17.0/w/w polyethylene glycol 40 hydrogenated castor oil;
  about 26.0% w/w caprylocaproyl polyoxyl-8 glycerides;
  about 4.0% w/w linoleoyl polyoxyl-6 glycerides; and
  about 0.4% w/w alpha tocopherol, wherein the composition forms an emulsion having an average globule size of about 201 nanometers when dispersed in an aqueous medium.

In another embodiment, the present invention is directed to a method of treating a disease selected from Prader-Willi syndrome, obesity, graft versus host disease, gelastic seizures/hypothalamic hamartoma, neonatal seizures, dystonia, central pain syndromes, phantom limb pain, multiple sclerosis, traumatic brain injury, radiation therapy, acute graft versus host disease, chronic graft versus host disease, T-cell autoimmune disorders, colitis, Dravet Syndrome, Lennox Gastaut Syndrome, mycolonic seizures, juvenile mycolonic epilepsy, refractory epilepsy, childhood absence epilepsy, schizophrenia, juvenile spasms, West syndrome, infantile spasms, refractory infantile spasms, tuberous sclerosis complex, brain tumors, neuropathic pain, *cannabis* use disorder, post-traumatic stress disorder, anxiety, early psychosis, Alzheimer's Disease, autism, acne, Parkinson's disease, social anxiety disorder, depression, diabetic retinopathy, diabetic nephropathy, diabetic neuropathy, ischemic injury of heart, ischemic injury of brain, chronic pain syndrome, and rheumatoid arthritis comprising administering a composition of the present invention to a subject in need thereof.

In another embodiment, the present invention is directed to a method of treating withdrawal symptoms comprising administering a composition of the present invention to a subject in need thereof, wherein the withdrawal symptoms are caused by the subject reducing or quitting use of an opioid, cocaine, heroin, an amphetamine or nicotine.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

As used herein "% w/w" and "percent w/w" refer to the percent weight of the total formulation.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1—Preparation of Compositions of the Invention

TABLE 1

Compositions of the Invention

| % w/w | 1 | 2 | 3 | 4 | 5 |
|---|---|---|---|---|---|
| Cannabidiol | 20.5 | 30.5 | 20.4 | 10.2 | 10.0 |
| Ethanol | 12.0 | 12.0 | 12.0 | 12.0 | 12.0 |
| Propylene Glycol | 9.0 | 8.0 | 10.0 | 10.0 | — |
| PEG 40 hydrogenated castor oil | 17.1 | 13.0 | 17.2 | 13.0 | 40.0 |
| Polyglyceryl-3 dioleate | 4.7 | 5.2 | 2.3 | 2.3 | 12.0 |
| Caprylocaproyl polyoxyl-8 glycerides | 26.0 | 19.5 | 25.5 | 26.0 | 3.0 |
| Linoleoyl polyoxyl-6 glycerides | 4.3 | 6.5 | — | — | 23.0 |
| C8/C10 medium chain triglycerides | — | — | 9.5 | 23.4 | — |
| Alpha-tocopherol (Vitamin E) | 0.4 | 0.3 | 0.3 | 0.3 | — |
| Polysorbate 80 | 6.0 | 5.0 | 2.8 | 2.8 | — |

Cremophor® RH40 was used as the source for polyethylene glycol 40 hydrogenated castor oil and is a registered trademark of and available from BASF SE corporation.

Plurol® Oleique CC 497 was used as the source of polyglyceryl-3 dioleate and is a registered trademark of and available from Gattefosse SAS.

Labrasol® was used as the source of caprylocaproyl polyoxyl-8 glycerides and is a registered trademark of and available from Gattefosse SAS.

Labrafil® M 2125 CS was used as the source of linoleoyl polyoxyl-6 glycerides and is a registered trademark of and available from Gattefosse SAS.

Miglyol® 812 was used as the source of C8/C10 medium chain triglycerides and is a registered trademark of and available from Cremer Oleo GMBH & Co.

Method

Alpha-tocopherol and cannabidiol were dissolved in ethanol to create a mixture while mixing. Propylene glycol was then added to this mixture followed by rest of the excipients and mixed well. Polyethylene glycol ("PEG") 40 hydrogenated castor oil was melted before being added to the mixture. Emulsification time and globule size was measured. Emulsification time is the time it takes 1 gram of the composition to completely disperse in about 200 milliliters of 0.1 N HCl solution while stirring. Globule size is measured using Nicomp ZLS Z3000.

TABLE 2

Emulsification time and globule size

| | Emulsification Time (min) | Globule Size (nm) |
|---|---|---|
| Composition 1 | <1 | 201.1 ± 112.65 |
| Composition 2 | <1 | 563.7 ± 525.95 |
| Composition 3 | <1 | 291.9 ± 196.36 |
| Composition 4 | <1 | 216.1 ± 66.32 |
| Composition 5 | 12 | 34.5 ± 9.8 |

Results

Compositions 1-4 emulsified in less than 1 minute. Composition 5 took 12 minutes to emulsify. Compositions 1, 3 and 4 created an emulsion having an average globule size of from 201.1 to 291.9 nanometers upon emulsification. Composition 2 created an emulsion having an average globule size of 563.7 nanometers upon emulsification. Composition 5 created an emulsion having an average globule size of 34.5 nanometers.

Example 2—Stability of Composition 6

TABLE 3

Composition 6

| % w/w | 6 |
|---|---|
| Cannabidiol | 18.18 |
| Ethanol | 14.0 |
| PEG 40 hydrogenated castor oil | 34.67 |
| Polyglyceryl-3 dioleate | 9.0 |
| Caprylocaproyl polyoxyl-8 glycerides | 3.0 |
| Linoleoyl polyoxyl-6 glycerides | 21.0 |
| Alpha-tocopherol (Vitamin E) | 0.05 |
| Ascorbyl palmitate | 0.1 |

Method

Composition 6 from Table 3, above, was prepared as in Example 1, above, and subjected to 40° C.±2° C. and 75±5% relative humidity ("RH") for 2 months and 25° C.±2° C. and 60±5% RH for 3 months. Results can be seen in Tables 4 and 5, below.

TABLE 4

Stability of Composition 6 at 40° C. ± 2° C. and 75 ± 5% RH

| | RRT | T = 0 | 1 Month | 2 Month |
|---|---|---|---|---|
| Physical appearance | | Clear, yellow colored | Clear, yellow colored | Clear, yellow colored |
| Assay (% of Initial Conc.) | | 100.00 | 96.37 | 94.24 |
| Delta 9-tetra-hydrocannabinol | 1.761 | 0.01% | 0.01% | 0.01% |
| Trans-(1R,6R)-3'-methyl-cannabidiol | 1.865 | 0.04% | 0.03% | 0.03% |
| Unknown Impurity | 0.319 | ND | 0.01% | 0.02% |
| | 0.373 | ND | ND | 0.01% |
| | 0.390 | ND | ND | 0.01% |
| | 0.436 | ND | ND | 0.02% |
| | 0.459 | ND | 0.02% | 0.05% |
| | 0.479 | ND | 0.02% | 0.06% |
| | 0.500 | 0.01% | 0.05% | 0.16% |
| | 0.592 | ND | 0.01% | ND |
| | 0.681 | ND | ND | 0.01% |
| | 0.771 | 0.05% | 0.05% | 0.05% |
| | 0.789 | ND | 0.02% | 0.06% |
| | 0.819 | 0.02% | 0.02% | 0.01% |
| | 0.825 | ND | ND | 0.01% |
| | 0.848 | ND | ND | 0.01% |
| | 2.075 | ND | 0.01% | ND |
| Total Impurities | | 0.08% | 0.21% | 0.48% |

RRT denotes relative retention time

TABLE 5

Stability of Composition 6 at 25° C. ± 2° C. and 60 ± 5% RH

| | RRT | T = 0 | 1 Month | 2 Month | 3 Month |
|---|---|---|---|---|---|
| Physical appearance | | Clear, Pale yellow | Clear, Pale yellow | Clear, Pale yellow | Clear, Pale yellow |
| Assay (% of Initial Conc.) | | 100.00 | 98.58 | 96.90 | 96.31 |
| Delta 9-tetra-hydrocannabinol | 1.761 | 0.01% | 0.01% | 0.01% | 0.01% |
| Trans-(1R,6R)-3'-methyl-cannabidiol | 1.865 | 0.04% | 0.03% | 0.03% | 0.03% |
| Cis-cannabidiol | 1.453 | 0.01% | 0.01% | 0.01% | 0.01% |
| Unknown Impurity | 0.313 | ND | ND | 0.01% | 0.01% |
| | 0.374 | ND | ND | ND | 0.02% |
| | 0.396 | ND | 0.01% | ND | ND |
| | 0.452 | ND | ND | ND | 0.01% |
| | 0.481 | ND | ND | ND | 0.01% |
| | 0.500 | 0.01% | 0.01% | 0.01% | 0.01% |
| | 0.771 | 0.05% | 0.05% | 0.05% | 0.06% |
| | 0.819 | 0.02% | 0.02% | 0.02% | 0.02% |
| | 2.075 | ND | 0.01% | ND | ND |
| Total Impurities | | 0.08% | 0.10% | 0.09% | 0.14% |

ND denotes not detected

As seen in Tables 4 and 5, Composition 6 had only 0.48% total impurities after 2 months at 40° C. and 0.14% total impurities after 3 months at 25° C. Thus, compositions of the present invention are stable.

Example 3. Pharmacokinetic Study in Dogs

Method

In-vivo bioavailability and pharmacokinetics of Composition 5 was evaluated in Beagle dogs. Specifically, five male Beagle dogs weighing from about 5 to about 11 kilograms were fasted overnight before dosing. Each Beagle dog was then administered 200 milligrams of cannabidiol in the form of Composition 5. Blood samples were collected at 0, 15 and 30 minutes and 1, 2, 3, 4, 8, 12, 24, 48, 72 and 96 hours after dosing.

Figure 2:
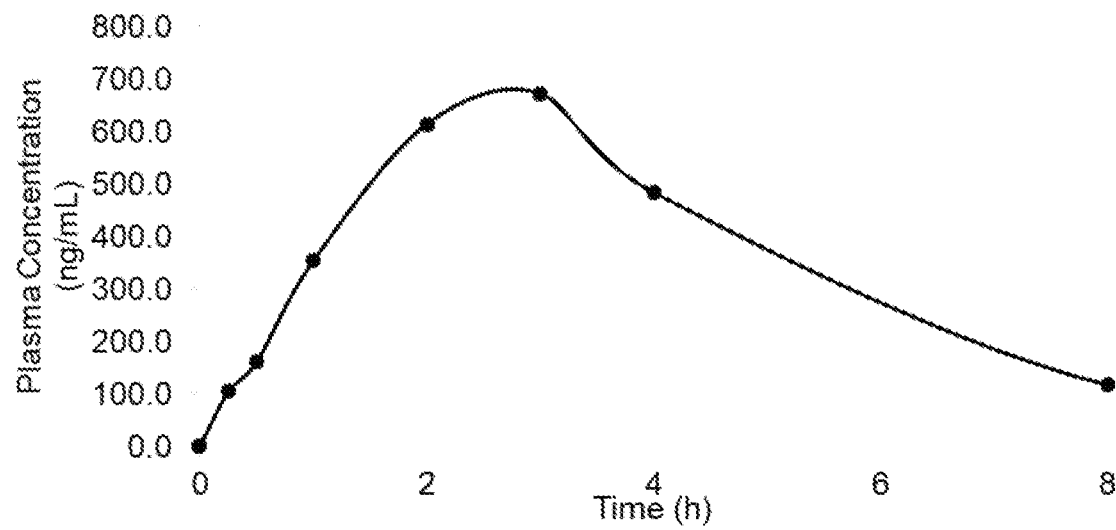
FIG. 2. Shows an illustration of plasma concentration of cannabidiol after administration of Composition 5 from time 0 to 8 hours.

The following pharmacokinetic parameters were calculated: peak concentration in plasma ("$C_{max}$"), time to peak concentration ("$T_{max}$") and area under the concentration-time curve ("AUC"). Results of this study can be seen in Table 6, below and in FIGS. 1 and 2.

TABLE 6

| Pharmacokinetic parameters | | |
|---|---|---|
| Cmax (ng/mL) | | 672.84 ± 400.68 |
| Tmax (h) | | 3 |
| AUC (ng/mL*h) | 0-1 h | 175.0 ± 76.8 |
| | 0-4 h | 1881 ± 952.7 |
| | 0-12 h | 3448.9 ± 1936.3 |
| | 0-24 h | 3971.0 ± 2250.9 |
| | 0-48 h | 4446.5 ± 2488.8 |
| | 0-96 h | 4910.8 ± 2750.1 |

Results

As seen in Table 6, Composition 5 provided a $C_{max}$ of 672.84 nanograms per milliliter ("ng/mL") and a $T_{max}$ of 3 hours. Further, Composition 6 provided an AUC of 175.0 at 1 hour, 1,881 at 4 hours, 3448.9 at 12 hours, 3971.0 at 24 hours, 4446.5 at 48 hours and 4910.8 at 96 hours.

Benefits, other advantages, and solutions to problems have been described herein with regard to specific embodiments. Furthermore, the connecting lines shown in various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article or apparatus that comprises a list of elements does not include only those elements but may include other elements not expressly listed or inherent to such process, method or article, or apparatus.

What is claimed is:

1. A self-emulsifying cannabidiol composition consisting essentially of
    from about 5% to about 35% w/w cannabidiol,
    from about 40% to about 99% w/w of one or more surfactants,
    from about 0.1% to about 2% w/w of an antioxidant, and
    one or more cosolvents selected from the group consisting of propylene glycol, polyethylene glycol, and ethanol,
    which does not comprise sesame oil, castor oil, olive oil, or water, and wherein the composition,
    (i) forms an emulsion having an average globule size from about 30 to about 600 nanometers in less than 30 minutes when dispersed in gastric fluid, and
    (ii) has the pharmacokinetic profile between 0 and 8 hours shown in FIG. 2 following a single oral administration of said composition to beagle dogs at a dose equivalent to 200 mg cannabidiol.

2. The self-emulsifying composition of claim 1, wherein said one or more surfactants is selected from the group consisting of polyethylene glycol 40 hydrogenated castor oil, caprylocaproyl polyoxyl-8 glycerides, linoleoyl polyoxyl-6 glycerides, polyglyceryl-3 dioleate, and polysorbate 80.

3. The self-emulsifying composition of claim 1, further consisting essentially of one or more oils selected from the group consisting of glyceryl monolinoleate, glyceryl monooleate, propylene glycol dicaprylocaprate, glycerol monostearate 40-55, and a medium chain triglyceride.

4. The self-emulsifying composition of claim 1, wherein said antioxidant is selected from the group consisting of alpha tocopherol, butylated hydroxy anisole, butylated hydroxy toluene, ascorbyl palmitate, ascorbic acid, sodium ascorbate, sodium metabisulfite, EDTA, citric acid, sodium bisulfite, sodium thiosulfate, thioglycerol, and propyl gallate.

5. The self-emulsifying composition of claim 1, wherein the composition is contained in a hard gelatin or soft gelatin capsule.

6. A method of treating a disease selected from the group consisting of Prader-Willi syndrome, obesity, graft versus host disease, gelastic seizures/hypothalamic hamartoma, neonatal seizures, dystonia, central pain syndromes, phantom limb pain, multiple sclerosis, traumatic brain injury, acute graft versus host disease, chronic graft versus host disease, T-cell autoimmune disorders, colitis, Dravet Syndrome, Lennox Gastaut Syndrome, mycolonic seizures, juvenile mycolonic epilepsy, refractory epilepsy, childhood absence epilepsy, schizophrenia, juvenile spasms, West syndrome, infantile spasms, refractory infantile spasms, tuberous sclerosis complex, brain tumors, neuropathic pain, *cannabis* use disorder, post-traumatic stress disorder, anxiety, early psychosis, Alzheimer's Disease, autism, acne, Parkinson's disease, social anxiety disorder, depression, diabetic retinopathy, diabetic nephropathy, diabetic neuropathy, ischemic injury of heart, ischemic injury of brain, chronic pain syndrome, and rheumatoid arthritis comprising administering a self-emulsifying composition of claim 1 to a subject in need thereof.

7. A method of treating withdrawal symptoms comprising administering a self-emulsifying composition of claim 1 to a subject in need thereof.

8. The method of claim 7, wherein the withdrawal symptoms are caused by the subject reducing or quitting use of an opioid, cocaine, heroin, an amphetamine or nicotine.

9. A method of reducing the use of an opioid, cocaine, heroin, an amphetamine, or nicotine, comprising administering a self-emulsifying composition of claim 1 to a subject in need thereof.

10. A self-emulsifying cannabidiol composition consisting essentially of
   from about 5% to about 35% w/w cannabidiol,
   from about 40% to about 99% w/w of a surfactant, and,
   from about 0.1% to about 2% w/w of an antioxidant, and
   one or more cosolvents selected from the group consisting of propylene glycol, polyethylene glycol, and ethanol,
   which does not comprise sesame oil, castor oil, olive oil, or water, and wherein the composition,
   (i) forms an emulsion having an average globule size from about 30 to about 600 nanometers in less than 30 minutes when dispersed in gastric fluid, and
   (ii) has a pharmacokinetic profile in which the single mean plasma concentration peak for cannabidiol has an area under the curve $(AUC)_{0-8}$ of about 3448 ng-hr/mL, Cmax of about 673 ng/mL, and a Tmax of about 3 hours, following a single oral administration of said composition to beagle dogs at a dose equivalent to 200 mg cannabidiol.

11. The self-emulsifying composition of claim 10, wherein said surfactant is selected from the group consisting of polyethylene glycol 40 hydrogenated castor oil, caprylocaproyl polyoxyl-8 glycerides, linoleoyl polyoxyl-6 glycerides, polyglyceryl-3 dioleate, and polysorbate 80.

12. The self-emulsifying composition of claim 10, further consisting essentially of one or more oils selected from the group consisting of glyceryl monolinoleate, glyceryl monooleate, propylene glycol dicaprylocaprate, glycerol monostearate 40-55, and a medium chain triglyceride.

13. The self-emulsifying composition of claim 10, wherein said surfactant is selected from the group consisting of alpha tocopherol, butylated hydroxy anisole, butylated hydroxy toluene, ascorbyl palmitate, ascorbic acid, sodium ascorbate, sodium metabisulfite, EDTA, citric acid, sodium bisulfite, sodium thiosulfate, thioglycerol, and propyl gallate.

14. The self-emulsifying composition of claim 10, wherein the composition is contained in a hard gelatin or soft gelatin capsule.

15. A method of treating a disease selected from the group consisting of Prader-Willi syndrome, obesity, graft versus host disease, gelastic seizures/hypothalamic hamartoma, neonatal seizures, dystonia, central pain syndromes, phantom limb pain, multiple sclerosis, traumatic brain injury, acute graft versus host disease, chronic graft versus host disease, T-cell autoimmune disorders, colitis, Dravet Syndrome, Lennox Gastaut Syndrome, mycolonic seizures, juvenile mycolonic epilepsy, refractory epilepsy, childhood absence epilepsy, schizophrenia, juvenile spasms, West syndrome, infantile spasms, refractory infantile spasms, tuberous sclerosis complex, brain tumors, neuropathic pain, *cannabis* use disorder, post-traumatic stress disorder, anxiety, early psychosis, Alzheimer's Disease, autism, acne, Parkinson's disease, social anxiety disorder, depression, diabetic retinopathy, diabetic nephropathy, diabetic neuropathy, ischemic injury of heart, ischemic injury of brain, chronic pain syndrome, and rheumatoid arthritis comprising administering a self-emulsifying composition of claim 10 to a subject in need thereof.

16. A method of treating withdrawal symptoms comprising administering a self-emulsifying composition of claim 10 to a subject in need thereof.

17. The method of claim 16, wherein the withdrawal symptoms are caused by the subject reducing or quitting use of an opioid, cocaine, heroin, an amphetamine or nicotine.

18. A method of reducing the use of an opioid, cocaine, heroin, an amphetamine, or nicotine, comprising administering a self-emulsifying composition of claim 10 to a subject in need thereof.

* * * * *